(12) United States Patent
Dalgleish et al.

(10) Patent No.: US 6,699,483 B1
(45) Date of Patent: Mar. 2, 2004

(54) CANCER TREATMENTS (75) Inventors: Angus George Dalgleish, London (GB); Peter Michael Smith, London (GB); Andrew Derek Sutton, London (GB); Anthony Ian Walker, London (GB)

(73) Assignee: Onyvax Limited, London (GB)

(*) Notice: Subject to any disclaimer, the term of this patent is extended or adjusted under 35 U.S.C. 154(b) by 0 days.

(21) Appl. No.: 09/857,690

(22) PCT Filed: Dec. 9, 1999

(86) PCT No.: PCT/GB99/04135

§ 371 (c)(1),
(2), (4) Date: Sep. 7, 2001

(87) PCT Pub. No.: WO00/33870

PCT Pub. Date: Jun. 15, 2000

(30) Foreign Application Priority Data

Dec. 10, 1998 (GB) .............................................. 9827103

(51) Int. Cl.$^7$ .............................................. A61K 35/12
(52) U.S. Cl. ................................. 424/277.1; 424/93.21; 424/93.3
(58) Field of Search ............................ 424/93.2, 93.21, 424/93.3, 277.1, 93.1; 435/325, 455; 514/44, 55; 536/23.1, 23.5; 530/395, 351, 350

(56) References Cited

FOREIGN PATENT DOCUMENTS

| WO | WO97/24132 | 7/1997 |
| WO | WO97/282255 | 8/1997 |

OTHER PUBLICATIONS

Marble, Michelle, Cancer Weekly Plus, p4(2), Nov. 24, 1997.*
Moran, Mark American Medical News, 42, 39, 23, Oct. 18, 1999.*
Brenner et al., Journal of Urology, 1995, p1575–1579 abstract only.*
Gorelik et al., Journal of Supramolecular Struct 12, 1979, p 385–402 abstract only.*
Bright et al., Cancer Research (57)(1): 995–1002 (1997).
Monahan et al., Proceedings of the 89th Annual Meeting of the American Association for Cancer Research, vol. 39, pp. 262–263 (1998) (Abstract #1795).
Diederichsen et al., Oncology Reports 5: 823–826 (1998).
Dillman et al., Cancer Biotherapy & Radiopharmaceuticals 15(2): 161–168 (2000).
Engel et al., Scand. J. Immunol. 45: 463–470 (1997).
Esparaza et al., J. of Immnology 131(5): 2117–2121 (1983).
Fenton et al., J. of Immunotherapy 19(5): 364–374 1996).
Fogel et al., J. Natl. Cancer Inst. 62(3):585–588 (1979).
Hrouda et al., BJU International 86: 742–748 (2000).
Jäger et al., Int. J. Cancer 71: 142–147 (1997).
Kayaga et al., Gene Therapy 6: 1475–1481 (1999).
Kusumoto et al., Cancer Immunol Immunother 50: 373–381 (2001).
Lehner et al., Cancer Immunol Immunother 32: 173–178 (1990).
Schreiber et al., Human Gene Therapy 10: 983–993 (1999).
Tamura et al., Science 278: 117–120 (1997).
Vermorken et al., The Lancet 353: 345–350 (1999).
Volpe, Cancer Genet Cytogenet 34: 125–134 (1988).

* cited by examiner

*Primary Examiner*—Mary E. Mosher
*Assistant Examiner*—Misook Yu
(74) *Attorney, Agent, or Firm*—Heller Ehrman White & McAuliffe (57) ABSTRACT

The invention relates to a product comprised of specific combinations of cell lines intended for use as an allogeneic immunotherapy agent for the treatment of prostate cancer in humans. The heterogeneity of the immunotherapeutic matches the heterogeneity of the antigenic profile in the target prostate cancer and immunises the recipients with many of the potential TAA and TSA which are expressed at various stages of the disease. The invention discloses a vaccine comprising a combination of three different cell lines prepared from primary or metastatic prostate cancer biopsy material. The cell lines are lethally irradiated utilising gamma irradiation at 50–300 Gy to ensure that they are replication incompetent.

24 Claims, 5 Drawing Sheets

Figure 1
T-Cell Proliferation Data for Patient Numbers 202 and 205

Figure 2 Western Blot Analysis of Serum From Patients 201 and 203

Patient 201 Pre-vaccination

Patient 201 Post Vaccination

Patient 203 Pre Vaccination

Patient 203 Post Vaccination

1= Molecular weight markers, 2= PNT2 lysate, 3= 1542 lysate, 4=DU145 lysate, 5=LnCap lysate

Figure 4 PSA Data for Patients 201 and 208

Patient 201

Patient 208

First dose administered at the first time point.

CANCER TREATMENTS

This application is a 371 of PCT/GB99/04135 filed on Dec. 9, 1999, which is hereby incorporated by reference.

FIELD OF THE INVENTION

This invention is concerned with agents for the treatment of primary, metastatic and residual cancer in mammals (including humans) by inducing the immune system of the mammal or human afflicted with cancer to mount an attack against the tumour lesion. In particular, the invention pertains to the use of whole-cells, derivatives and portions thereof with or without vaccine adjuvants and/or other accessory factors. More particularly, this disclosure describes the use of particular combinations of whole-cells and derivatives and portions thereof that form the basis of treatment strategy.

BACKGROUND TO THE INVENTION

It is known in the field that cancerous cells contain numerous mutations, qualitative and quantitative, spatial and temporal, relative to their normal, non-cancerous counterparts and that at certain periods during tumour cells' growth and spread a proportion of these are capable of being recognised by the hosts' immune system as abnormal. This has led to numerous research efforts world-wide to develop immunotherapies that harness the power of the hosts' immune system and direct it to attack the cancerous cells, thereby eliminating such aberrant cells at least to a level that is not life-threatening (reviewed in Maraveyas, A. & Dalgleish, A. G. 1977 *Active immunotherapy for solid tumours in vaccine design* in The Role of Cytokine Networks, Ed. Gregoriadis et al., Plenum Press, New York, pages 129–145; Morton, D. L. and Ravindranath, M. H. 1996 *Current concepts concerning melanoma vaccines* in Tumor Immunology—Immunotherapy and Cancer Vaccines, ed. Dalgleish, A. G. and Browning, M., Cambridge University Press, pages 241–268. See also other papers in these publications for further detail).

Numerous approaches have been taken in the quest for cancer immunotherapies, and these can be classified under five categories:

Non-specific Immunotherapy

Efforts to stimulate the immune system non-specifically date back over a century to the pioneering work of William Coley (Coley, W. B., 1894 Treatment of inoperable malignant tumours with toxins of erisipelas and the Bacillus prodigosus. Trans. Am. Surg. Assoc. 12: 183). Although successful in a limited number of cases (e g. BCG for the treatment of urinary bladder cancer, IL-2 for the treatment of melanoma and renal cancer) it is widely acknowledged that non-specific immunomodulation is unlikely to prove sufficient to treat the majority of cancers. Whilst non-specific immune-stimulants may lead to a general enhanced state of immune responsiveness, they lack the targeting capability and also subtlety to deal with tumour lesions which have many mechanisms and plasticity to evade, resist and subvert immune-surveillance.

Antibodies and Monoclonal Antibodies

Passive immunotherapy in the form of antibodies, and particularly monoclonal antibodies, has been the subject of considerable research and development as anti-cancer agents. Originally hailed as the magic bullet because of their exquisite specificity, monoclonal antibodies have failed to live up to their expectation in the field of cancer immunotherapy for a number of reasons including immune responses to the antibodies themselves (thereby abrogating their activity) and inability of the antibody to access the lesion through the blood vessels. To date, three products have been registered as pharmaceuticals for human use, namely Panorex (Glaxo-Welicome), Rituxan (IDEC/Genentech/Hoffman la Roche) and Herceptin (Genentech/Hoffman la Roche) with over 50 other projects in the research and development pipeline. Antibodies may also be employed in active immunotherapy utilising anti-idiotype antibodies which appear to mimic (in an immunological sense) cancer antigens. Although elegant in concept, the utility of antibody-based approaches may ultimately prove limited by the phenomenon of 'immunological escape' where a subset of cancer cells in a mammalian or human subject mutates and loses the antigen recognised by the particular antibody and thereby can lead to the outgrowth of a population of cancer cells that are no longer treatable with that antibody.

Subunit Vaccines

Drawing on the experience in vaccines for infectious diseases and other fields, many researchers have sought to identify antigens that are exclusively or preferentially associated with cancer cells, namely tumour specific antigens (TSA) or tumour associated antigens (TAA), and to use such antigens or fractions thereof as the basis for specific active immunotherapy.

There are numerous ways to identify proteins or peptides derived therefrom which fall into the category of TAA or TSA. For example, it is possible to utilise differential display techniques whereby RNA expression is compared between tumour tissue and adjacent normal tissue to identify RNAs which are exclusively or preferentially expressed in the lesion. Sequencing of the RNA has identified several TAA and TSA which are expressed in that specific tissue at that specific time, but therein lies the potential deficiency of the approach in that identification of the TAA or TSA represents only a "snapshot" of the lesion at any given time which may not provide an adequate reflection of the antigenic profile in the lesion over time. Similarly a combination of cytotoxic T lymphocyte (CTL) cloning and expression-cloning of cDNA from tumour tissue has lead to identification of many TAA and TSA, particularly in melanoma. The approach suffers from the same inherent weakness as differential display techniques in that identification of only one TAA or TSA may not provide an appropriate representation of a clinically relevant antigenic profile.

Over fifty such subunit vaccine approaches are in development for the treatment of a wide range of cancers, although none has yet received marketing authorisation for use as a human pharmaceutical product. In a similar manner to that described for antibody-based approaches above, subunit vaccines may also be limited by the phenomenon of immunological escape.

Gene Therapy

The majority of gene therapy trials in human subjects have been in the area of cancer treatment, and of these a substantial proportion have been designed to trigger and/or amplify patients' immune responses. Of particular note in commercial development are Allovectin-7 and Leuvectin, being developed by Vical Inc for a range of human tumours, CN706 being developed by Calydon Inc for the treatment of prostate cancer, and StressGen Inc.'s stress protein gene therapy for melanoma and lung cancer. At the present time, it is too early to judge whether these and the many other 'immuno-gene therapies' in development by commercial and academic bodies will ultimately prove successful, but it is widely accepted that commercial utility of these approaches are likely to be more than a decade away.

Cell-based Vaccines

Tumours have the remarkable ability to counteract the immune system in a variety of ways including: downregulation of the expression of potential target proteins; mutation of potential target proteins; downregulation of surface expression of receptors and other proteins; downregulation of MHC class I and II expression thereby disallowing direct presentation of TAA or TSA peptides; downregulation of co-stimulatory molecules leading to incomplete stimulation of T-cells leading to anergy; shedding of selective, non representative membrane portions to act as decoy to the immune system; shedding of selective membrane portions to anergise the immune system; secretion of inhibitory molecules; induction of T-cell death; and many other ways. What is clear is that the immunological heterogeneity and plasticity of tumours in the body will have to be matched to a degree by immunotherapeutic strategies which similarly embody heterogeneity. The use of whole cancer cells, or crude derivatives thereof, as cancer immunotherapies can be viewed as analogous to the use of whole inactivated or attenuated viruses as vaccines against viral disease. The potential advantages are:

(a) whole cells contain a broad range of antigens, providing an antigenic profile of sufficient heterogeneity to match that of the lesions as described above;

(b) being multivalent (i.e. containing multiple antigens), the risk of immunological escape is reduced (the probability of cancer cells 'losing' all of these antigens is remote); and (c) cell-based vaccines include TSAs and TAAs that have yet to be identified as such; it is possible if not likely that currently unidentified antigens may be clinically more relevant than the relatively small number of TSAs/TAAs that are known.

Cell-based vaccines fall into two categories. The first, based on autologous cells, involves the removal of a biopsy from a patient, cultivating tumour cells in vitro, modifying the cells through transfection and/or other means, irradiating the cells to render them replication-incompetent and then injecting the cells back into the same patient as a vaccine. Although this approach enjoyed considerable attention over the past decade, it has been increasingly apparent that this individually-tailored therapy is inherently impractical for several reasons. The approach is time consuming (often the lead time for producing clinical doses of vaccine exceeds the patients' life expectancy), expensive and, as a 'bespoke' product, it is not possible to specify a standardised product (only the procedure, not the product, can be standardised and hence optimised and quality controlled). Furthermore, the tumour biopsy used to prepare the autologous vaccine will have certain growth characteristics, interactions and communication with surrounding tissue that makes it somewhat unique. This alludes to a potentially significant disadvantage to the use of autologous cells for immunotherapy: a biopsy which provides the initial cells represents an immunological snapshot of the tumour, in that environment, at that point in time, and this may be inadequate as an immunological representation over time for the purpose of a vaccine with sustained activity that can be given over the entire course of the disease.

The second type of cell-based vaccine and the subject of the current invention describes the use of allogeneic cells which are be genetically (and hence immunologically) mismatched to the patients. Allogeneic cells benefit from the same advantages of multivalency as autologous cells. In addition, as allogeneic cell vaccines can be based on immortalised cell lines which can be cultivated indefinitely in vitro, thus this approach does not suffer the lead-time and cost disadvantages of autologous approaches. Similarly the allogeneic approach offers the opportunity to use combinations of cells types which may match the disease profile of an individual in terms of stage of the disease, the location of the lesion and potential resistance to other therapies.

There are numerous published reports of the utility of cell-based cancer vaccines (see, for example, Dranoff, G. et al. WO 93/06867; Gansbacher, P. WO 94/18995; Jaffee, E. M. et al. WO 97/24132; Mitchell, M. S. WO 90/03183; Morton, D. M. et al. WO 91/06866). These studies encompass a range of variations from the base procedure of using cancer cells as an immunotherapy antigen, to transfecting the cells to produce GM-CSF, IL-2, interferons or other immunologically-active molecules and the use of 'suicide' genes. Groups have used allogeneic cell lines that are HLA-matched or partially-matched to the patients' haplotype and also allogeneic cell lines that are mismatched to the patients' haplotype in the field of melanoma and also mismatched allogeneic prostate cell lines transfected with GM-CSF.

DESCRIPTION OF THE INVENTION

The invention disclosed here relates to a product comprised of specific combinations of cell lines intended for use as an allogeneic immunotherapy agent for the treatment of prostate cancer in humans. The heterogeneity of the immunotherapeutic described herein matches the heterogeneity of the antigenic profile in the target prostate cancer and immunises the recipients with many of the potential TAA and TSA which are expressed at various stages of the disease. The cell lines are chosen from appropriate cell lines which possess the following characteristics: the cells are immortalised, prostate or metastatic prostate in origin, show good growth in large scale cell culture, and are well characterised allowing for quality control and reproducible production of the component cell lines.

The invention disclosed herein also relates to a product comprising of a combination of cells lines described above whereby the cell lines are chosen to allow for the maximum mismatch of haplotype with the intended patient population, thereby ensuring the maximum allogeneic potential and subsequent immune response to the product.

The invention described discloses a vaccine comprising a combination of three different cell lines prepared from primary or metastatic prostate cancer biopsy material using methods known in the art (reviewed and cited in Rhim, J. S. and Kung, H-F., 1997 Critical Reviews in Oncogenesis 8(4):305–328) and/or selected from Group A (cell lines derived from primary prostate cancer lesions) and Group B (cell lines derived from metastatic prostate cancer lesions) listed in Table 1.

In one embodiment, the combination of cell lines consists of three different cell lines derived from primary prostate cancer lesions.

In another embodiment, the combination consists of two different cell lines derived from primary prostate cancer lesions and one cell line derived from a metastatic prostate cancer lesion.

In another embodiment, the combination consists of one cell line derived from a primary prostate cancer lesion combined with two different cell lines derived from metastatic prostate cancer lesions.

In a further embodiment, the combination consists of three different cell lines derived from metastatic prostate cancer lesions.

The cell lines are lethally irradiated utilising gamma irradiation at 50–300 Gy to ensure that they are replication incompetent.

The cell lines and combinations referenced above, to be useful as immunotherapy agents must be frozen to allow transportation and storage, therefore a further aspect of the invention is any combination of cells referenced above formulated with a cryoprotectant solution. Suitable cryoprotectant solutions may include but are not limited to, 10–30% v/v aqueous glycerol solution, 5–20% v/v dimethyl sulphoxide or 5–20% w/v human serum albumin may be used either as single cryoprotectants or in combination.

TABLE 1

| Group A | Group B |
| --- | --- |
| NIH1519-CPTX, NIH1532-CP2TX, NIH1535-CP1TX and NIH1542-CP3TX (immortalised lines derived from primary prostate cancers by Dr. Suzanne Topalian at the NIH; these cell lines have been described in Cancer Research, vol 57 (5), pp 995–1002 and have been deposited at ATCC for patent purposes) CA-HPV-10 (ATCC Number: CRL-2220) | DU145 (ATCC Number: HTB-81) LnCap (ATCC Number: CRL-1740 and CRL-10995) PC3 (ATCC Number: CRL-1435) |

A further embodiment of the invention is the use of the cell line combinations with non-specific immune stimulants such as BCG or M. Vaccae, Tetanus toxoid, Diphtheria toxoid, Bordetella Pertussis, interleukin 2, intedeukin 12, interleukin 4, interleukin 7, Complete Freund's Adjuvant, Incomplete Freund's Adjuvant or other non-specific agents known in the art. The advantage is that the general immune stimulants create a generally enhanced immune status whilst the combinations of cell lines, both add to the immune enhancement through their haplotype mismatch and target the immune response to a plethora of TAA and TSA as a result of the heterogeneity of their specific origins.

The invention will now be described with reference to the following examples, and the Figures.

EXAMPLE 1

Growth, Irradiation, Formulation and Storage of Cells

An immortalised cell line derived from primary prostate tissue, namely NIH1542-CP3TX, was grown in roller bottle culture in KSFM medium supplemented with 25 µg/ml bovine pituitary extract, 5 ng/ml of epidermal growth factor, 2 mM L-glutamine, 10 mM HEPES buffer and 5% foetal calf serum (FCS) (hereinafter called "modified KSFM") following recovery from liquid nitrogen stocks. Following expansion in T175 static flasks the cells were seeded into roller bottles with a growth surface area of 1,700 cm$^2$ at 2–5×10$^7$ cells per roller bottle.

Two metastasis-derived cell lines were also used, namely LnCap and Du145 both of which were sourced from ATCC. LnCap was grown in large surface area static flasks in RPMI medium supplemented with 10% FCS and 2 mM L-glutamine following seeding at 1–10×10$^6$ cells per vessel and then grown to near confluence. Du145 was expanded from frozen stocks in static flasks and then seeded into 850 cm$^2$ roller bottles at 1–20×10$^7$ cells per bottle and grown to confluence in DMEM medium containing 10% FCS and 2 mM L-glutamine.

All cell lines were harvested utilising trypsin at 1× normal concentration. Following extensive washing in DMEM the cells were re-suspended at a concentration of 10—40×10$^6$ cells/ml and irradiated at 50–300 Gy using a Co$^{60}$ source. Following irradiation the cells were formulated in cryopreservation solution composed of 10% DMSO, 8% human serum albumin in phosphate buffered saline, and frozen at a cell concentration of 15–50×10$^6$ cells/ml by cooling at a rate of 1° C. per minute and then transferred into a liquid nitrogen freezer until required for use.

Vaccination

Prostate cancer patients were selected on the basis of being refractory to hormone therapy with a serum PSA level of 30 ng/ml. Ethical permission and MCA (UK Medicines Control Agency) authorisation were sought and obtained to conduct this trial in 15 patents.

The vaccination schedule was as follows:

| Dose Number | Cell Lines Administered |
| --- | --- |
| 1, 2 and 3 | NIH1542-CP3TX (24 × 10$^6$ cells per dose) |
| 4 and subsequent | LnCap/Du145/NIH1542 (8 × 10$^6$ cells of each cell line per dose) |

The cells were warmed gently in a water bath at 37° C. and admixed with mycobacterial adjuvant prior to injection into patients. Injections were made intra-dermally at four injection sites into draining lymph node basins. The minimum interval between doses was two weeks, and most of the doses were given at intervals of four weeks. Prior to the first dose, and prior to some subsequent doses, the patients were tested for delayed-type hypersensitivity (DTH) against the three cell lines listed in the vaccination schedule above and also against PNT2 (an immortalized normal prostate epithelial cell line sourced from ECACC) (all tests involved 0.8×10$^6$ cells with no adjuvant).

Analysis of Immunological Response (a) T-Cell Proliferation Responses

To determine if vaccination resulted in a specific expansion of T-cell populations that recognised antigens derived from the vaccinating cell lines we performed a proliferation assay on T-cells following stimulation with lysates of the prostate cell lines. Whole blood was extracted at each visit to the clinic and used in a BrdU (bromodeoxyuridine) based proliferation assay as described below:

Patient BrdU Proliferation Method

| Reagents | | |
|---|---|---|
| RPMI | | Life Technologies, Paisley Scotland. |
| BrdU | | Sigma Chemical Co, Poole, Dorset. |
| PharMlyse | 35221E | Pharmingen, Oxford UK |
| Cytofix/Cytoperm | 2090KZ | " |
| Perm/Wash buffer (×10) | 2091KZ | " |
| FITC Anti-BrdU/Dnase | 340649 | Becton Dickinson |
| PerCP Anti-CD3 | 347344 | " |
| Pe Anti-CD4 | 30155X | Pharmingen |
| Pe Anti-CD8 | 30325X | " |
| FITC mu-IgG1 | 349041 | Becton Dickinson |
| PerCP IgG1 | 349044 | " |
| PE IgG1 | 340013 | " |

Method

1) Dilute 1 ml blood with 9 ml RPMI+2mM L-gin +PS +50 $\mu$M 2-Me. Do not add serum. Leave overnight at 37° C.
2) On following morning, aliquot 450 $\mu$l of diluted blood into wells of a 48-well plate and add 50 $\mu$l of stimulator lysate. The lysate is made by freeze-thawing tumour cells ($2\times10^6$ cell equivalents/ml)×3 in liquid nitrogen and then storing aliquots frozen until required.
3) Culture cells at 37° C. for 5 days
4) On the evening of day 5 add 50 $\mu$l BrdU@30 $\mu$g/ml
5) Aliquot 100 $\mu$l of each sample into a 96-well round-bottomed plate.
6) Spin plate and discard supernatant
7) Lyse red cells using 100 $\mu$l Pharmlyse for 5 minutes at room temperature
8) Wash ×2 with 50 $\mu$l of Cytofix
9) Spin and remove supernatant by flicking
10) Permeabilise with 100 $\mu$l Perm wash for 10 mins at RT
11) Add 30 $\mu$l of antibody mix comprising antibodies at correct dilution made up to volume with Perm-wash
12) Incubate for 30 mins in the dark at room temperature.
13) Wash ×1 and resuspend in 100 $\mu$l 2% paraformaldehyde
14) Add this to 400 $\mu$l FACSFlow in cluster tubes ready for analysis
15) Analyse on FACScan, storing 3000 gated CD3 events.

96-well plate for stimulation

|  | Nil | ConA | 1542 | LnCap | Du145 | Pnt2 |
|---|---|---|---|---|---|---|
| PBL 1 | | | | | | |
| PBL 2 | | | | | | |
| PBL 3 | | | | | | |
| PBL 4 | | | | | | |
| PBL 5 | | | | | | |
| PBL 6 | | | | | | |

| PBL 1 | | PBL 2 | | PBL 3 | | PBL 4 | | PBL 5 | | PBL 6 | |
|---|---|---|---|---|---|---|---|---|---|---|---|
| Nil A | 15 D | Nil A | 15 D | Nil A | 15 D | Nil A | 15 D | Nil A | 15 D | Nil A | 15 D |
| Nil D | 15 E | Nil D | 15 E | Nil D | 15 E | Nil D | 15 E | Nil D | 15 E | Nil D | 15 E |
| Nil E | Ln D | Nil E | Ln D | Nil E | Ln D | Nil E | Ln D | Nil E | Ln D | Nil E | Ln D |
| Con D | Ln E | Con D | Ln E | Con D | Ln E | Con D | Ln E | Con D | Ln E | Con D | Ln E |
| Con E | Du D | Con E | Du D | Con E | Du D | Con E | Du D | Con E | Du D | Con E | Du D |
| | Du E | | Du E | | Du E | | Du E | | Du E | | Du E |
| | Pn D | | Pn D | | Pn D | | Pn D | | Pn D | | Pn D |
| | Pn E | | Pn E | | Pn E | | Pn E | | Pn E | | Pn E |

Figure 1:
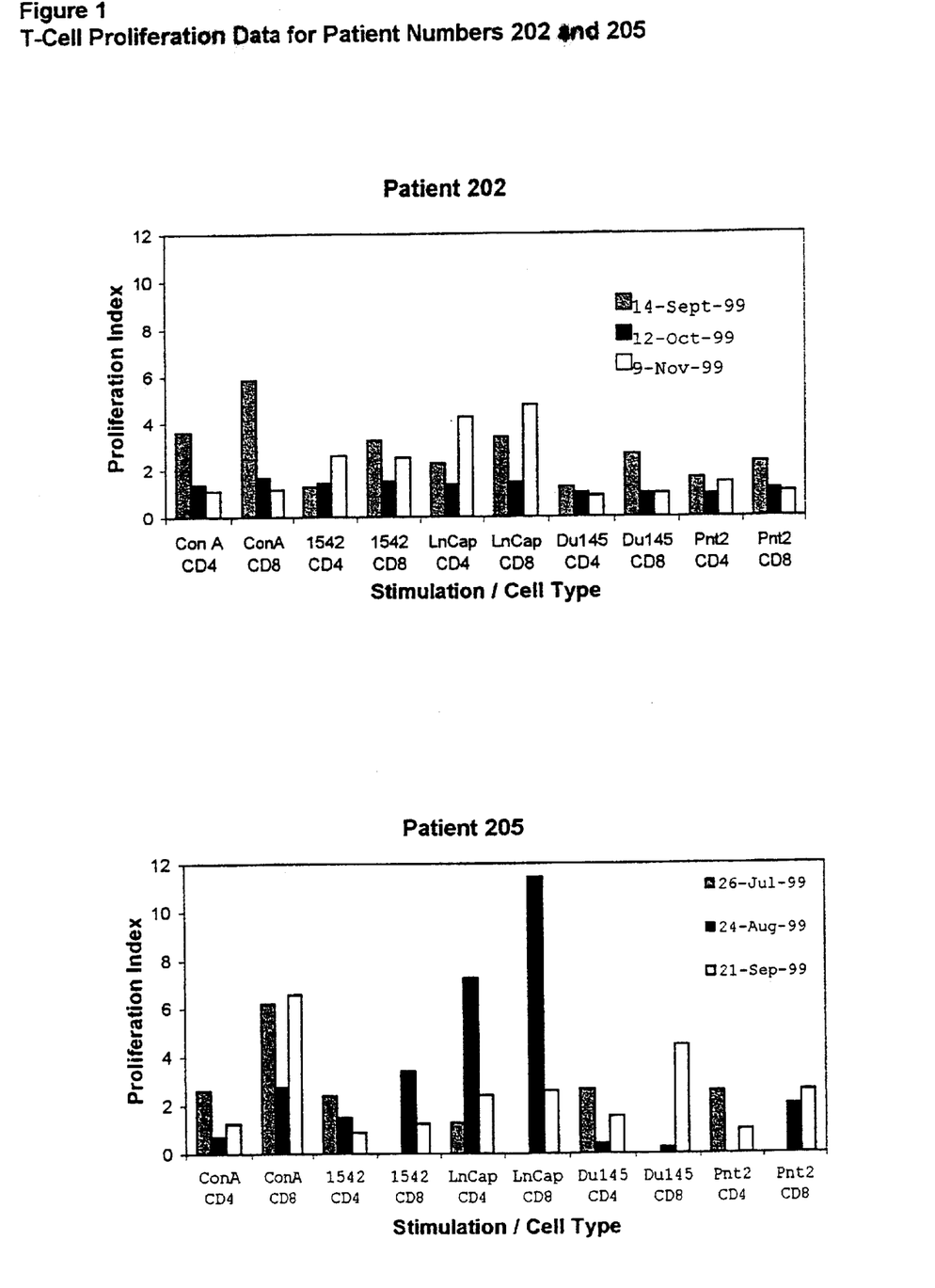
FIG. 1 shows T-cell proliferation data for Patient Nos. 202 and 205.

Legend:
A: IgG1-FITC (5 $\mu$l)  IgG1-PE (5 $\mu$l)  IgG1-PerCP (5 $\mu$l)
   15 $\mu$l MoAb + 15 $\mu$l
D: BrdU-FITC (5 $\mu$l)  CD4-PE (5 $\mu$l)  CD3-PerCP (5 $\mu$l)
   15 $\mu$l MoAB + 15 $\mu$l
E: BrdU-FITC (5 $\mu$l)  CD8-PE (5 $\mu$l)  CD3-PerCP (5 $\mu$l)
   15 $\mu$l MoAb + 15 $\mu$l
15: NIH1542-CP3TX
Ln: LnCap
D: Du145
Pn: PNT2
Con: ConA lectin (positive control)
Nil: No stimulation The results for the proliferation assays are shown in FIG. 1 where a proliferation index for either CD4 or CD8 positive T-cells are plotted against the various cell lysates, the proliferation index being derived by dividing through the percentage of T-cells proliferating by the no-lysate control.

Results are shown for patient numbers 202 and 205. Results are given for four cell lysates namely, NIH1542, LnCap, DU-145 and PNT-2 (an immortalised normal prostate epithelial cell line). Overall, 50% of patients treated mount a specific proliferative response to NIH1542-CP3TX, LnCap and DU-145 to a degree and in some cases also to PNT-2.

(b) Western Blots Utilising Patients' Serum

Standardised cell lysates were prepared for a number of prostate cell lines to enable similar quantites of protein to be loaded on a denaturing SDS PAGE gel for Western blot analysis. Each blot was loaded with molecular weight markers, and equal amounts of protein derived from cell lysates of NIH1542, LnCap, DU-145 and PNT-2. The blot was then probed with serum from patients derived from pre-vaccination and following 16 weeks vaccination (four to six doses).

Method a) Sample Preparation (Prostate Tumor Lines)
   Wash cell pellets 3 times in PBS
   Re-suspend at $1\times10^7$ cells/ml of lysis buffer Pass through 5 cycles of rapid freeze thaw lysis in liquid nitrogen/water bath Centrifuge at 1500 rpm for 5 min to remove cell debris Ultracentrifuge at 20,000 rpm for 30 min to remove membrane contaminants Aliquot at 200 µl and stored at −80° C.

b) Gel Electrophoresis

Lysates mixed 1:1 with Laemelli sample buffer and boiled for 5 min

20 µg samples loaded into 4–20% gradient gel wells

Gels run in Bjerrum and Schafer-Nielson transfer buffer (with SDS) at 200 V for 35 min.

c) Western Transfer

Gels, nitrocellulose membranes and blotting paper equilibrated in transfer buffer for 15 min Arrange gel-nitrocellulose sandwich on anode of semi-dry electrophoretic transfer cell: 2 sheets of blotting paper, nitrocellulose membrane, gel, 2 sheets of blotting paper Apply cathode and run at 25 V for 90 min.

d) Immunological Detection of Proteins

Block nitrocellulose membranes ovenight at 4° C. with 5% Marvel in PBS/0/05% Tween 20

Figure 2:
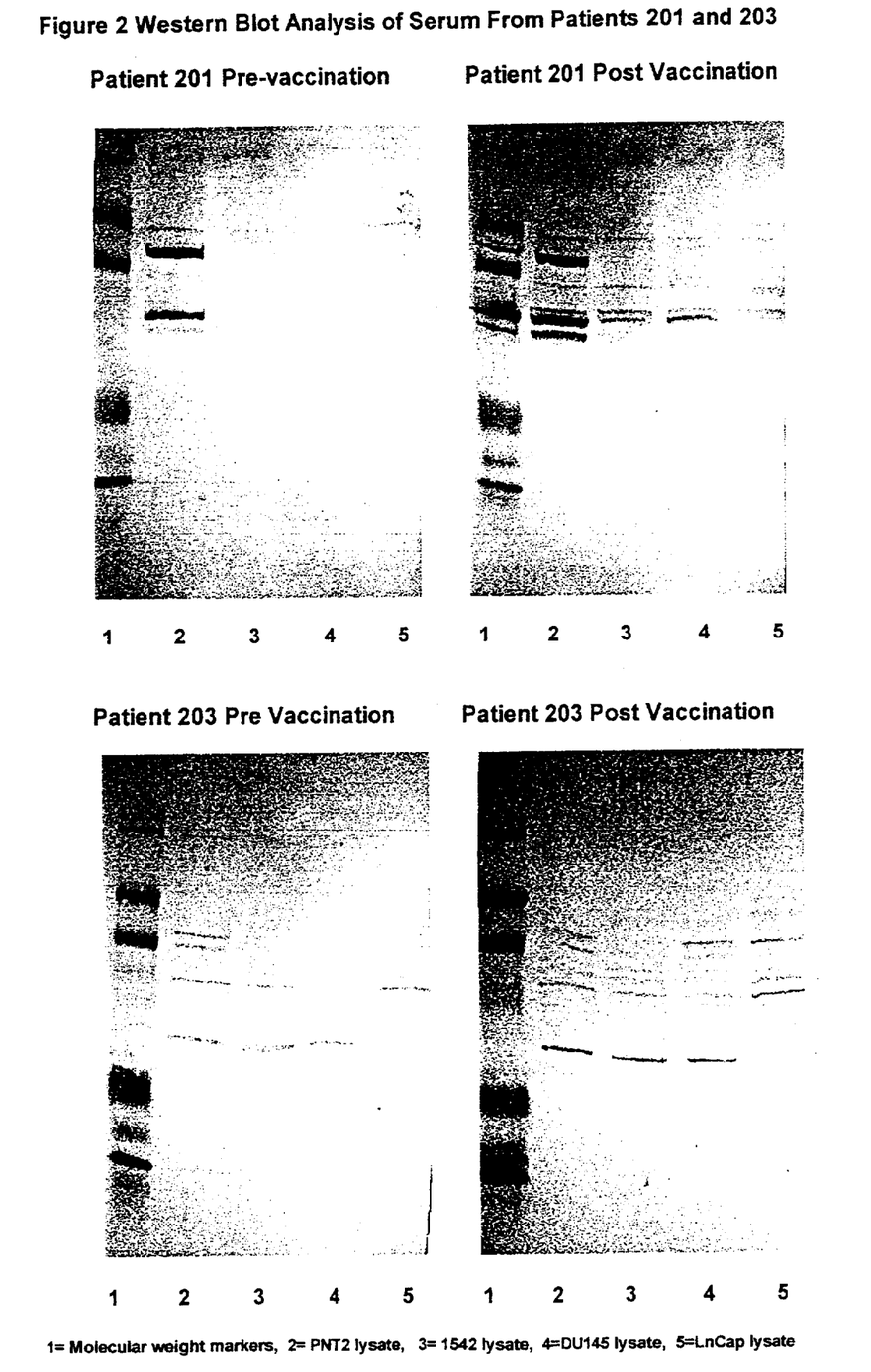
FIG. 2 shows Western Blot analysis of serum from Patient Nos. 201 and 203.

Rinse membranes twice in PBS/0.05% Tween 20, then wash for 20 min and 2×5 min at RT on a shaking platform Incubate membranes in 1:20 dilution of clarified patient plasma for 120 min at RT on a shaking platform Wash as above with an additional 5 min final wash Incubate membranes in 1:250 dilution of biotin anti-human IgG or IgM for 90 min at RT on a shaking platform Wash as above with an additional 5 min final wash Incubate membranes in 1:1000 dilution of streptavidin-horseradish peroxidase conjugate for 60 min at RT on a shaking platform Wash as above Incubate membranes in Diaminobenzidine peroxidase substrate for 5 min to allow colour development, stop reaction by rinsing membrane with water Results of Western blots probed with anti-IgG second antibodies for patients 201 and 203 are shown in FIG. 2. The Figure shows baseline and week 16 time points for each patient with four cell lysates on each blot.

Overall in patients who received at least four to six doses, over 50% showed an increase in intensity of bands present before vaccination and/or a broadening of the number of bands being recognised by the serum.

Of particular note is the reactivity of serum from patients 201 and 203 towards the PNT2 lysate which did not form part of the vaccination regime (other than DTH testing), but nevertheless appears to share common antigens with NIH1542, LnCap and DU145 in both patients serum.

(c) Antibody Titre Determination

Antibody titres were determined by coating ELISA plates with standardised cell line lysates and performing dilution studies on serum from patients vaccinated with the cell lines.

Method for ELISA with anti-lysate IgG.

1. Coat plates with 50 µl/well lysates (@10 µg/ml) using the following dilutions:

| Lysate | Protein conc | Coating conc | amount/ml | amount in 5 mls µl |
|---|---|---|---|---|
| PNT2 | 2.5 mg/ml | 10 µg/ml | 3.89 µl | 19.4 µl |
| 1542 | 4.8 mg/ml | 10 µg/ml | 2.07 µl | 10.3 µl |
| Du145 | 2.4 mg/ml | 10 µg/ml | 4.17 µl | 20.8 µl |
| LnCap | 2.4 mg/ml | 10 µg/ml | 4.12 µl | 20.6 µl |

2. Cover and incubate overnight@4° C.

3. Wash ×2 PBS-Tween. Pound plate on paper towels to dry.

4. Block with PBS/10% FCS (100 µl/well)

5. Cover and incubate@room temperature for 1 hour (minimum).

6. Wash ×2 PBS-Tween

7. Add 100 µl PBS-10% FCS to rows 2–8

8. Add 200 µl plasma sample (diluted 1 in 100 in PBS-10% FCS ie. 10 µl plasma added to 990 µls PBS-10% FCS) to row 1 and do serial 100 µl dilutions down the plate as below. Discard extra 100 µl from bottom well. Cover and incubate in fridge overnight.

9. Dilute biotinylated antibody (Pharmingen; IgG 34162D) ie. final conc 1 mg/ml (ie 20 ml in 10 mls).

10. Cover and incubate@RT for 45min.

11. Wash ×6 as above.

12. Dilute streptavidin —HRP (Pharmingen, 13047E 0; dilute 1:1000 (ie 10 ml →10 mls).

13. Add 100 ml/well.

14. Incubate 30 min@RT.

15. Wash ×8.

16. Add 100 ml substrate/well. Allow to develop 10–80 min at RT.

17. Colour reaction stopped by adding 100 ml 1M H2SO4.

18. Read OD@A405nm.

Figure 3:
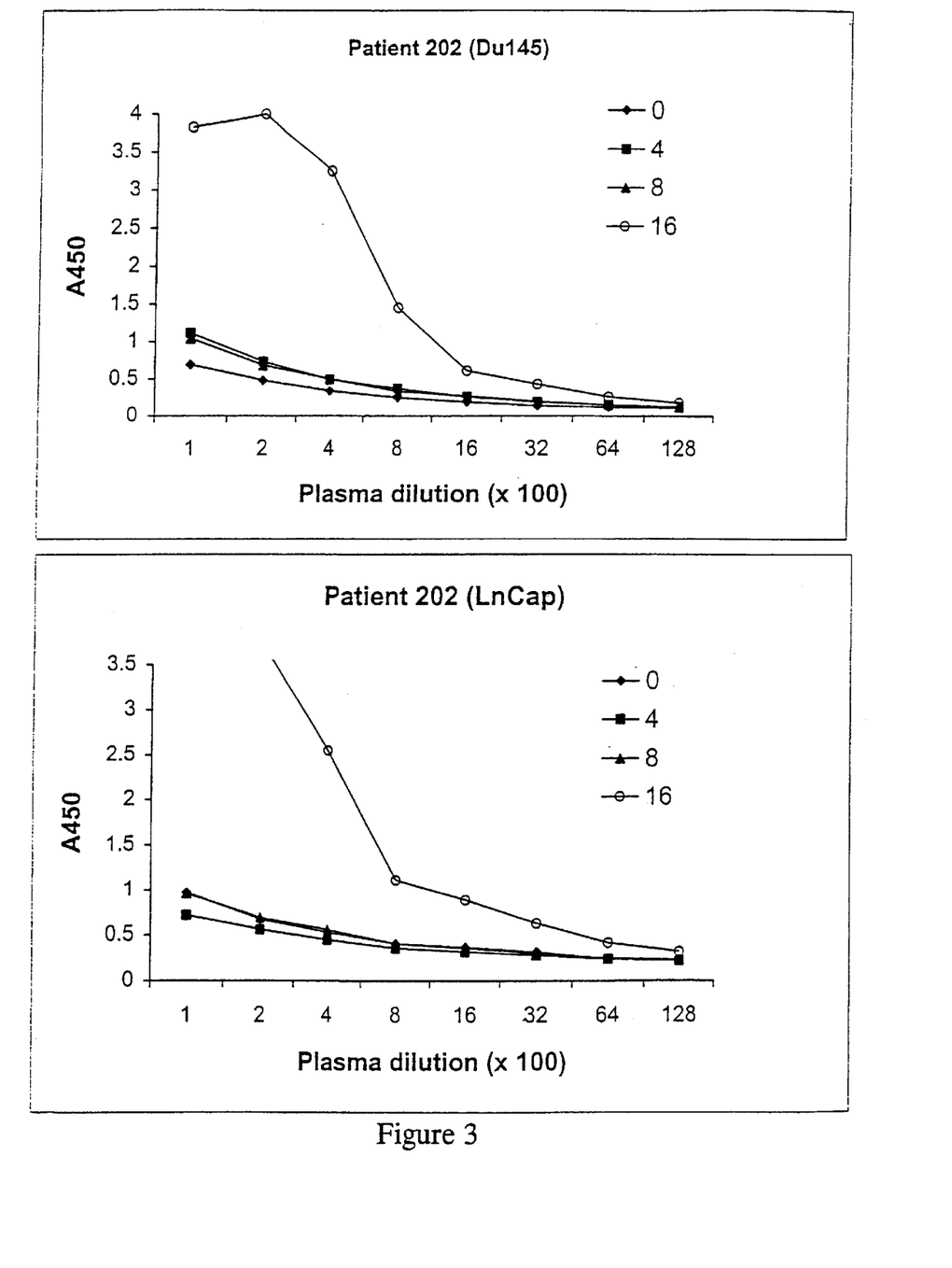
FIG. 3 shows Antibody Titres of serum from Patient No. 201.

The results (FIG. 3) show that after vaccination with at least four to six doses, patients can show an increase in antibody titre against cell line lysates.

(d) Evaluation of PSA Levels

Figure 4:
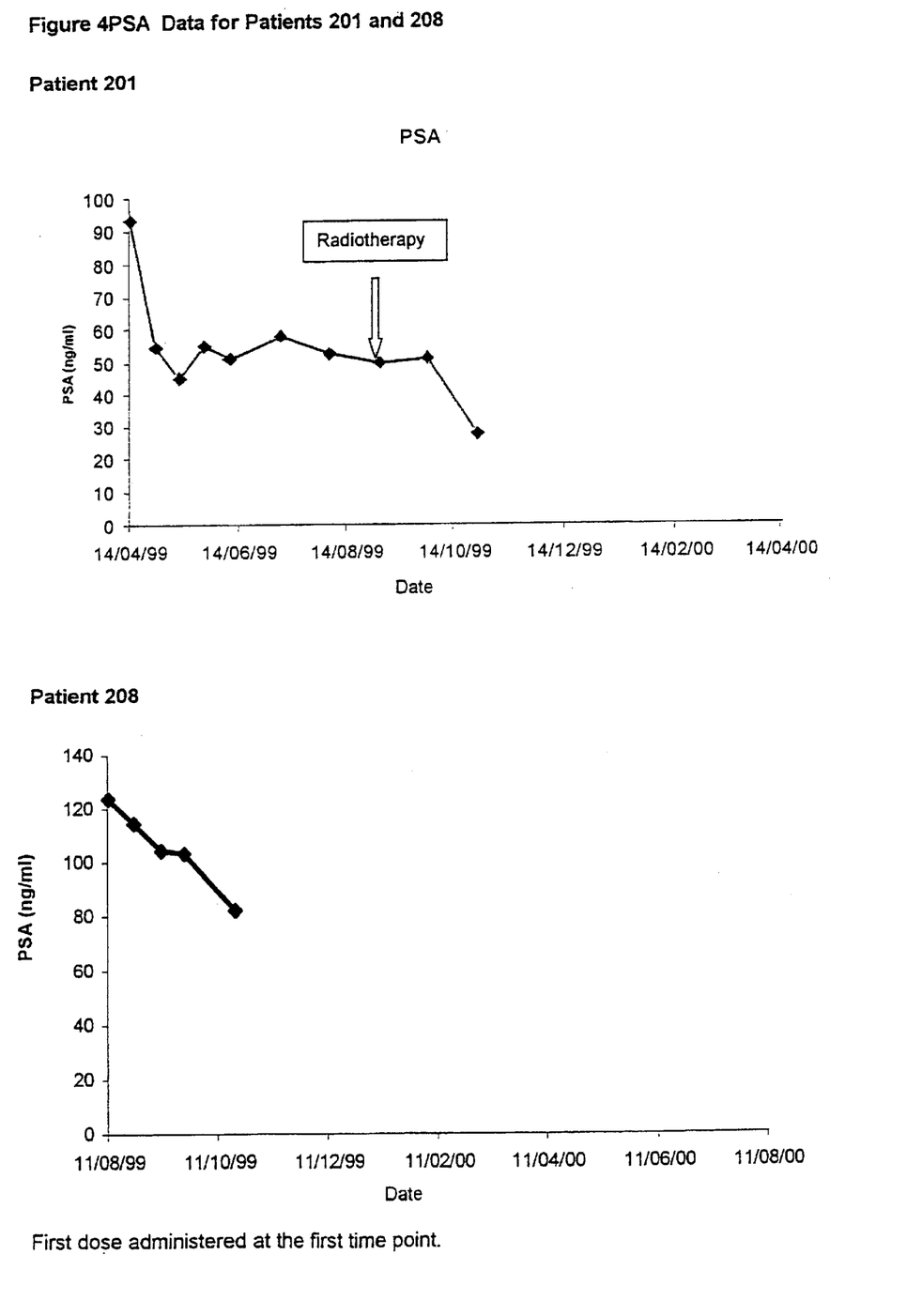
FIG. 4 shows PSA data for Patients 201 and 208.

PSA levels for patients receiving the vaccine were recorded at entry into the trial and throughout the course of vaccination, using routinely used clinical kits. The PSA values for patients 201 and 208 are shown in FIG. 4 and portray a drop or stabilisation of the PSA values, which in this group of patients usually continues to rise, often exponentially. The result for patient 201 is somewhat confounded by the radiotherapy treatment to alleviate bone pain, although the PSA level had dropped significantly prior to radiotherapy.

EXAMPLE 2

The invention can also be applied to earlier stage prostate cancer patients, and the immunotherapy can also be administered through different routes. As an example, the following protocol can be used:

Cells are grown, irradiated, formulated and stored according to the methods described in Example 1. Prostate cancer patients are selected prior to radical prostatectomy and are vaccinated with a combination of three irradiated cell lines ($8 \times 10^6$ cells per line) three times at two week intervals prior to surgery. Approximately half of the patients are vaccinated intradermally into four draining lymph node basins (cell lines mixed with mycobacterial adjuvant for at least the first dose); remaining patients are injected intra-prostatically, with intradermal mycobacterial adjuvant administered at a distant site for at least the first dose. Biopsy samples of the prostate removed by surgery are examined for prostate cell death and the presence of infiltrating immune cells. In addition, T-cell function, Western blot analysis and antibody titres are determined according to the method of Example 1. Serum PSA is also measured at intervals in these patients.

Following this protocol, immunological responses can be detected. In addition, death of prostate cells can be detected in surgical biopsies.

What is claimed is:

1. An allogeneic immunotherapeutic agent for the treatment of prostate cancer comprising three human prostate tumor cell lines of which one cell line is derived from a primary tumor and the other two cell lines are derived from metastatic tissue.

2. An allogeneic immunotherapeutic agent for the treatment of prostate cancer comprising a mixture of three human prostate tumor cell lines, wherein one cell line is derived from a primary tumor and the other two cell lines are derived from two different metastatic tissues.

3. An allogeneic immunotherapeutic agent for the treatment of prostate cancer comprising a mixture of three human prostate tumor cell lines, wherein three cell lines are derived from three different primary tumors.

4. An allogeneic immunotherapeutic agent for the treatment of prostate cancer comprising a mixture of three human prostate tumor cell lines, wherein two cell lines are derived from one or two primary tumor(s) and the other cell line is derived from a metastatic tissue.

5. An allogeneic immunotherapeutic agent for the treatment of prostate cancer comprising a mixture of three human prostate tumor cell lines, wherein three cell lines are derived from metastatic tissues.

6. An allogeneic immunotherapeutic agent for the treatment of prostate cancer comprising a mixture of three human prostate tumor cell lines, wherein three cell lines are derived from two or three different metastatic tissues.

7. An immunotherapeutic agent of claim 1, wherein the tumor cell lines derived from metastatic tissue and are selected from the group consisting of LnCap, DU145 and PC3.

8. An immunotherapeutic agent of claim 1, wherein the tumor cell lines have been irradiated at 50 to 300 Gy.

9. An immunotherapeutic agent of claim 1, wherein the tumor cell lines have been irradiated at 100 to 150 Gy.

10. An allogeneic immunogenic composition comprising an immunotherapeutic agent of claim 1 combined with a vaccine adjuvant selected from the group consisting of BCG, *M. Vaccae*, Tetanus toxoid, Diphtheria toxoid, *Bordetella Pertussis*, interteukin 2, interleukin 12, interleukin 4, interleukin 7, Complete Freund's Adjuvant, Incomplete Freund's Adjuvant, and a nonspecific adjuvant.

11. An immunogenic composition comprising an immunotherapeutic agent of claim 1 combined with a vaccine adjuvant, wherein the adjuvant is a mycobacterial preparation.

12. An immunotherapeutic agent of claim 1, wherein the cells are formulated with a cryoprotectant solution including at least one selected from the group consisting of 10–30% v/v aqueous glycerol solution, 5–20% v/v dimethyl sulphoxide and 5–20% w/v human serum albumin.

13. An immunotherapeutic agent of claim 1, wherein the cells are formulated with a cryoprotectant solution comprising 5–20% v/v dimethyl sulphoxide and 5–20% w/v human serum albumin in combination.

14. An immunotherapeutic agent of claim 1, wherein said agent is capable of inducing an immune response in patients by activation of immune T-cells.

15. An immunotherapeutic agent of claim 1, wherein said agent is capable of inducing an immune response in patients by induction of antibody production.

16. An immunotherapeutic agent of claim 1, wherein said agent is capable of inducing a decrease in the rate of rise or a decline in the level of serum PSA in prostate cancer patients.

17. An immunotherapeutic agent according to claim 1, wherein said agent is capable of being administered intradermally.

18. An immunotherapeutic agent according to claim 1, wherein said agent is capable of being administered intraprostatically.

19. An allogeneic immunotherapeutic vaccine composition for the treatment of prostate cancer, wherein said composition comprises an agent according to claim 1 and a physiologically acceptable agent selected from the group consisting of excipient, adjuvant and carrier.

20. An allogeneic method of prophylaxis or treatment of prostate cancer by administering to a patient an effective amount of an agent according to claim 1.

21. An allogeneic immunotherapeutic agent for the treatment of prostate cancer comprising three different human prostate tumor cell lines, wherein one cell line is derived from a primary prostate tumor and the other two cell lines are derived from metastatic prostate tissue.

22. The allogeneic immunotherapeutic agent of claim 21, where the cell lines are selected so as to maximize haplotype mismatch.

23. An allogeneic immunotherapeutic agent for the treatment of prostate cancer comprising three different human prostate tumor cell lines, wherein one cell line is derived from a metastatic prostate tissue and the other two cell lines are derived from primary prostate tumors.

24. The allogeneic immunotherapeutic agent of claim 23, where the cell lines are selected so as to maximize haplotype mismatch.

\* \* \* \* \*